United States Patent [19]

Brill et al.

[11] Patent Number: 4,504,468

[45] Date of Patent: Mar. 12, 1985

[54] METHOD AND COMPOSITION FOR CONTROL OF TERMITE AND SHIPWORMS

[75] Inventors: Winston J. Brill; William C. von Meyer, both of Madison, Wis.

[73] Assignee: Agracetus, Middleton, Wis.

[21] Appl. No.: 514,936

[22] Filed: Jul. 18, 1983

[51] Int. Cl.³ .............................................. A01N 59/16
[52] U.S. Cl. .................................. 424/147; 424/131; 424/DIG. 11
[58] Field of Search ................. 424/131, 147, DIG. 11

[56] References Cited

U.S. PATENT DOCUMENTS

| | | | |
|---|---|---|---|
| 2,025,405 | 12/1935 | Vessle | 424/131 |
| 2,784,139 | 3/1957 | Cutler | 424/347 |
| 2,886,486 | 5/1959 | Depew | 424/145 |
| 3,070,495 | 12/1962 | Esenther et al. | 424/DIG. 11 |
| 3,214,332 | 10/1965 | Hoehwait | 424/131 |
| 3,290,343 | 12/1966 | Stone et al. | 260/429 |
| 3,317,571 | 5/1967 | Werner et al. | 260/429 |
| 3,832,463 | 8/1974 | Nicholson | 424/131 |
| 3,993,752 | 11/1976 | Stutz | 424/129 |
| 4,132,780 | 1/1979 | McConnell | 414/127 |
| 4,363,798 | 12/1982 | D'Orazia | 424/DIG. 11 |

FOREIGN PATENT DOCUMENTS 800568  8/1958  United Kingdom ............... 424/131

OTHER PUBLICATIONS

The Merck Index, 9th Ed. (1976), pp. 1117, 1123 and 809.
Pienkos et al.; J. of Bacteriology, 2/81, pp. 743-751, vol. 145, No. 2.
Nagatani et al.; Bioch. et Biophys. Acta, 362, 160-166, (1974).

*Primary Examiner*—Allen J. Robinson
*Attorney, Agent, or Firm*—Isaksen, Lathrop, Esch, Hart & Clark

[57] ABSTRACT

A composition and method for control of animal pests capable of nitrogen fixation is disclosed in which the active ingredient is a metal compound of either molybdenum or tungsten. It is disclosed that such metal salts of molybdenum and tungsten are uniquely toxic to termites and shipworms in low dosages. The composition can be incorporated into direct control agents, termite baits, soil inoculants, or may be incorporated with other ingredients in a wood treating dip or pressure treating composition for wood preservation.

13 Claims, No Drawings

METHOD AND COMPOSITION FOR CONTROL OF TERMITE AND SHIPWORMS

CROSS-REFERENCE TO RELATED APPLICATION

This application is a continuation-in-part of Ser. No. 431,564 filed Sept. 30, 1982, now abandoned.

TECHNICAL FIELD

The present invention is in the field of methods and compositions for the control of animals capable of nitrogen fixation in general, and particularly for the control of termites and shipworms.

BACKGROUND OF THE INVENTION

While the present invention is broadly directed toward animals capable of nitrogen fixation, it is particularly useful in the control of termites. The prior art is generally cognizant of a wide variety of compounds which are useful either for introduction into wood for preserving the wood fiber from terminate infestation, of for directly controlling termites. Wood infestation and destruction by termites is a widely recognized problem, particularly in tropical and sub-tropical areas of the world and much research has been directed toward methods and compositions for controlling termite activity. Generally, in the prior art, it has been the practice to use either general organic insecticides or toxic metallic compounds to control or to kill termites. These compositions may be utilized directly to control termites by incorporated in a bait or attractant composition, but are typically utilized by injection or saturation in wood members so as to preserve wood which may come in contact with termite colonies.

Exemplary of the prior art illustrating the use of general organic insecticides against termites is the disclosure of U.S. Pat. No. 3,070,495, which describes the use of a decayed wood extract as a termite attractant so that the termites can be controlled by a conventional general organic insecticide, such as DDT, dieldrin, chlordane, parathion, malathion or others. Other examples are known in the art of packaging techniques for including such organic pesticides in baits, traps, or other devices intended to attract termites.

The use of several metallic compounds have been proposed or disclosed for termite control. U.S. Pat. No. 2,784,139 discloses a composition for preserving wood including, as a mycocidal and insecticidal ingredient, one of a variety of metal compounds including chromated zinc chloride, copper sulphate, arsenic compounds, and mercury compounds. Similarly U.S. Pat. No. 2,886,486 discloses a wood impregnating compound including therein chromated zinc sulphate. More recently, the disclosure of U.S. Pat. No. 3,832,463 illustrates the use of hexavalent chromium in a wood treating composition intended to preserve wood from microbial and insecticidal activity. It has also been proposed, in accordance with the disclosure of U.S. Pat. No. 3,993,752, to utilize an alkali metal cyanide added to a liquid fungicide including organic or inorganic sales of mercury, lead, tin, copper, or zinc to provide a wood treating composition having fungicidal and bactericidal properties. Further, it has been disclosed, in U.S. Pat. No. 4,132,780, that certain azide and metal salt formulations, including salts of iron, aluminum, nickel, maganese, colbalt, zinc, tin, or magnesium are capable of being used to control fungi and other micro-organisms.

It has been proposed, in one known teaching in the prior art, to utilize molybdenum in a composition claimed to have biological activity. In the disclosure of U.S. Pat. No. 2,025,405, a method for producing a water soluble colloidal molybdenum compound contains valuable "pharmaceutical and bacteriological" properties. In addition, U.S. Pat. Nos. 3,290,343 and 3,317,571 disclose certain compounds including molybdenum which are recited to be biologically active having use as pesticides.

It has been known and understood for some time that a very small number of animals, including termites and shipworms, are capable of nitrogen fixation, in a fashion analogous to the nitrogen fixation of legumes. The animals themselves actually do not fix nitrogen. Instead, it has been discovered that among the microflora living in symbiotic relationship in the gut of termites are some capable of nitrogen fixation and they supply nitrogen in a fixed form to the host termite for protein synthesis. For example, Benemann in "Nitrogen Fixation in Termites", *Science*, Volume 181, page 164, July 13, 1973, discusses the phenomenon of nitrogen fixation in termites and suggests that the nitrogen-fixing agent is the intestinal bacterial flora of the termites. It is assumed that these symbiotic bacteria in the termite gut play an essential role in the nutrition of these insects since the wood used as food for the termite is very low in nitrogen. Another pest species that lives in and feeds n wood is the shipworm, a mollusk that is responsible for significant damage to wood in marine environments. The shipworm also supports large numbers of nitrogen fixing bacteria in its intestines, Carpenter et al., "Nitrogen Fixation in Shipworms", *Science*, Volume 187, pps. 551–552, 1975.

It is known that among the nitrogen-fixing bacteria symbiotic with legumes, the enzyme nitrogenase, which is the enzyme responsible for nitrogen fixation, requires several atoms of molybdenum to be effective. It has been disclosed in literature that tungsten competes with molybdenum and may serve as an antagonist of molybdenum in the formation of this enzyme, Nagatani and Brill, "The Effect of Mo, W, and V on the Synthesis of Nitrogenase Components in *Azotobacter vinelandii*", *Bioch. et Biophys. Acta*, 362, 160–166 (1974).

SUMMARY OF THE INVENTION

The present invention is summarized in that a composition for control of nitrogen-fixing pests includes a pesticidal amount of an effectively soluble compound of a metal selected from the group consisting of molybdenum and tungsten.

An object of the present invention is to also provide a method for the control of wood pests such as termites and shipworms and for the preservation of wood in which wood is treated with a composition including a pesticidal amount of a metal compound wherein the metal is selected from a group consisting of molybdenum and tungsten.

It is an object of the present invention to provide a highly effective composition for termite and shipworm control which is economical to utilize and effective in its application.

It is also an object of the present invention to provide such a control composition for termites and shipworms to which the organisms have no avoidance mechanism such that they will not actively avoid treated material.

DETAILED DESCRIPTION OF THE INVENTION

Broadly stated, the present inventon envisions a pest control agent for pests capable of nitrogen fixation which may be administered directly to the pests, or which may be used to protect wood from termite or shipworm infestation, and which includes, as its active ingredient, a compound preferably a salt, of either or both of molybdenum or tungsten. These metal salts of molybdenum and tungsten exhibit pesticidal activity in concentrations as low as 500 parts per million (ppm) of the metal ingredient. The concentrations of these metals may be reduced even lower if a more gradual rate of kill is acceptable and may, of course be increased to higher concentrations if it is economically feasible. The molybdenum or tungsten compounds conveniently may be introduced to the pests by treating the wood upon which pests would otherwise feed, or by inclusion into a pellet or other bait which is deposited in a location which the pests would frequent. It is envisioned, in particular, that salts of these metallic elements may be incorporated into wood treating dips or impregnating compounds which may be introduced under pressure into wood in a conventional treatment process to inhibit termite or shipworm feeding on that wood.

The exact mechanism of molybdenum and tungsten toxicity on these organisms is not presently completely understood. The toxicity of tungsten was investigated under the thesis that tungsten would be an antagonist for the active metal cofactor of the enzyme nitrogenase, which is molybdenum. The enzyme nitrogenase is manufactured by the microflora in the gut of termites and shipworms. While the feeding of tungsten dosed cellulose to termites has proven toxic, it has been discovered unexpectedly in the course of the research on tungsten that small concentrations of molybdenum were equally, and, in some cases, even more toxic to termites than the dosages of tungsten. It is believed that either the termites, or more probably the microflora in their gut, include a biological "scavenging" mechanism specifically designed to isolate and absorb molybdenum from the environment. This same mechanism should exist in shipworms which feed on a similar diet. Since molybdenum is normally a relatively rare element in the diet of wood-eating organisms, providing these organisms with an excess supply of dietary molybdenum appears to cause the scavenging mechanism to introduce such a quantity of molybdenum into the animal's gut that the organisms die of molybdenum toxicity. It is believed that the tungsten toxicity to termites may be due either to the antagonistic activity of tungsten on the nitrogenase enzyme or to the molybdenum scavenging mechanism which might also accumulate tungsten. It is known, for example, that in some nitrogen fixing bacteria the mechanisms for molybdenum uptake also accumulate tungsten, "Molybdenum Accumulation and Storage in *Klebsiella pneumoniae* and *Azobacter vinelandii*, Pienkos and Brill, *Jour. of Bact.*, 145: 2 pp. 743-751. It is to be understood, however, that the hypothesis for the mechanism of toxicity of molybdenum and tungsten is unproven at this stage. It is also possible that other mechanisms may be responsible for the molybdenum toxicity disclosed here. For instance, it is conceivable that the highly reducing characteristic of the microflora environment in the animal gut may cause metal salt precipitation in the gut which may interfere with other metabolic processes.

In order to give those skilled in the art a better understanding of this invention and appreciation of the advantages of the compounds formulated in accordance with the present invention, the following illustrative experimental examples are given:

EXAMPLE 1

The termicidal toxicity of various molybdenum and tungsten compounds were compared against various controls by testing of identical sets of 60 termite larvae which were isolated in separate vials. All of the termite larvae were of the species *Reticulitermes flavipes* and were gathered from the wild in the around the area of Ingham County, Mich. Each of the groups of termites in the experiment were fed alpha-cellulose dosed with a solution containing the molybdenum, tungsten, or control salt dissolved in aqueous solution and formed into pellets. For low solubility compounds, a portion of the dosant was mixed as dry material in the pellets to complete the dosage amount. The pellets were, as indicated in the chart below, dosed with several test compounds. In each of the samples, the termites were observed over a period of thirty-two days or until the date at which 50% of the termites were killed due to chemical toxicity. Results of these experiments and observations are summarized in the following Table I:

TABLE I

| Dosant to the Alpha-Cellulose | Concentration of Metal p.p.m. wt/wt | Days to 50% Kill | Published Solubility in grams/100 cc |
| --- | --- | --- | --- |
| $H_2O$ (control) | — | >32 | — |
| $CaSO_4$ (control) | 3,000 (Ca) | >32 | .209 at 30° C. |
| no food (control) | — | 22 | — |
| $CaCl_2$ (control) | 2,600 (Ca) | >32 | — |
| $MoO_3$ | 4,000 (Mo) | 13 | .049 at 28° C. |
| $H_2MoO_4$ | 5,000 (Mo) | 13 | .133 at 18° C. |
| $CaMoO_4$ | 3,000 (Mo) | 22 | .0050 at 25° C. |
| $Na_2MoO_4$ | 5,000 (Mo) | 13 | 39.38 at 28° C. |
| $Na_2MoO_4$ | 500 (Mo) | 22 | 39.38 at 28° C. |
| $Na_2MoO_4$ | 50 (Mo) | >32 | 39.38 at 28° C. |
| $FeMoO_4$ | 3,600 (Mo) | 17 | .0076 at 25° C. |
| $Na_2WO_4$ | 9,000 (W) | 16 | 57.5 at 0° C. |
| $Na_2WO_4$ | 90 (W) | >32 | 57.5 at 0° C. |

Materials providing 50% mortality to the termites within the experimental period are considered to be active against termites. In the experimental samples in which a 50% kill was achieved during the 32 day span of the experiment, most of the remaining termites typically died shortly thereafter. Note that higher level of the toxic additives caused termite mortality well before the termites which were starved (no food control) died.

The symptoms of the molybdenum toxicity to the termites included that the abdomens of the termites turned blue-grey after a relatively short period, i.e. three days, of feeding on the dosed cellulose samples. No such phenomenon was observed with control termites or termites feeding on tungsten dosed pellets.

Also in the above experiment, in the sample of termites which were fed sodium molybdate at a concentration of 5000 p.p.m., the termites were also allowed access to pellets inoculated only with distilled water. The termites in this sample exhibited no avoidance of the molybdenum dosed pellets thus suggesting that termites would not be capable of avoiding molybdenum treated wood or cellulosic baits containing molybdenum or tungsten in their environment.

EXAMPLE II

To verify that the observed toxicity is attributable to molybdenum, and not simply to the presence of a metal salt, an additional test was run with a variety of metal salts. Two samples each of fifty individual *Reticulitermes flavipes* worker larvae were fed kraft paper pellets dosed with metal salts. The metal salt compounds were dosed onto the pellets by being dissolved in water and deposited on the paper. The temperature and environmental conditions were constant and the pellets were periodically moistened with water. Results of these tests for each of the following metal salts are summarized in Table II below:

TABLE II

| Dosant | Dosage (mg per 5 gram paper) | Days to 50% Kill | Percent Survival at 48 days |
|---|---|---|---|
| $NaNbO_3$ | 9.03 | — | 95 |
| $NaBiO_3$ | 14.80 | — | 88 |
| None (Control) | — | — | 91 |
| $NaVO_3$ | 6.50 | — | 58 |
| $Na_2B_4O_7.10H_2O$ | 19.80 | 8–10 | 0 |
| $CuCl_2.2H_2O$ | 9.38 | — | 81 |
| $Na_2MoO_4.2H_2O$ | 12.5 | 24–28 | 1 |
| $Na_2SnO_3.3H_2O$ | 13.9 | — | 89 |
| $CoCl_2.6H_2O$ | 12.4 | — | 83 |
| $Na_2WO_4.2H_2O$ | 17.30 | 37–49 | 19 |
| NaCl | 9.18 | — | 91 |
| $Fe_2(SO_4)_3.3H_2O$ | 12.20 | — | 93 |
| $SrCl_2.6H_2O$ | 13.90 | — | 88 |
| $FeCl_3.6H_2O$ | 14.30 | — | 90 |
| $MnCl_2.4H_2O$ | 10.30 | — | 92 |
| $NiSO_4.6H_2O$ | 13.90 | — | 62 |
| $TiO_4$ | 4.37 | — | 81 |
| $NH_4Al(SO_4)_2.12H_2O$ | 23.60 | — | 92 |
| $MgSO_4.7H_2O$ | 12.50 | — | 90 |
| $BaCl_2.2H_2O$ | 12.50 | — | 87 |
| NaI | 7.83 | 17–24 | 18 |
| $Ce(SO_4)_2.4H_2O$ | 21.50 | — | 92 |
| $NaTaO_3$ | 4.37 | — | 88 |
| LiCl | 2.20 | — | 86 |
| $ZnSO_4.7H_2O$ | 15.00 | — | 86 |

The amount of metal salt in each of the above samples was formulated to give an effective concentration of 1000 p.p.m. of metal in the termite food, with the exception of NaCl (dose tripled) and $Fe_2(SO_4)_3$ (dose cut by one-half). The kill rate of the boron compound was expected inasmuch as borate is a previously documented termiticidal (and general insecticidal) agent. However, borate is very soluble and not amenable to easy methods for making insoluble, and thus its effectiveness in wood treatment is very limited. The use of molybdenum does not suffer from such a limitation.

EXAMPLE III

To verify that a wide variety of molybdenum compounds are effective, another test was run using a variety of molybdenum and one tungsten compounds. The method of dosing the compounds onto the termite feed, again kraft paper pellets, varied according to the solubility of the compound. The more soluble compounds were introduced entirely in aqueous solution, while for some of the less soluble compounds part of the dosage included dry material added to the pellets. The molybdenum disulfide, which is absolutely insoluble in water, and the molybdenum were ground and added to the pellets only in granular form. The amount of metal compound in the paper pellets was selected to give a concentration of 500 p.p.m. of metal in the sample, escept for the $MoS_2$, which was at a dosage of 5000 p.p.m. A single sample of 60 termites was used for each sample, and the results are summarized in Table III below:

TABLE III

| Dosant | Number dead (of 60) at end of Four weeks | Published Solubility in grams per 100 cc |
|---|---|---|
| $H_2O$ (control) | 3 | — |
| $Na_2MoO_4$ | 20 | 39.38 (at 28° C.) |
| $(NH_4)_2Mo_2O_7$ | 13 | 43 (at 25° C.) |
| $H_2MoO_4$ | 16 | .133 (at 18° C.) |
| $MoO_3$ | 11 | .049 (at 28° C.) |
| Mo ore | 18 | — |
| $MoS_2$ | 0 | 0 (effectively insoluble) |
| $NaWO_4$ | 26 | 57.5 (at 0° C.) |
| $FeSO_4$ | 0 | — |
| $Na_2Cr_2O_7$ | 0 | 238 (at 0° C.) |

Again in this test the metal salts were dissolved in water and deposited on the paper in solution. The molybdenum ore, which was raw ore obtained from Climax Molybdenum Co., was unrefined ore from a sample designated 77-2A by Climax. The assay of the ore was represented to be 0.263% Mo and 2.15% $FeS_2$.

This test showed that a variety of very soluble and marginally soluble molybdenum compounds are effective termicidal agents, while the virtually insoluble molybdenum disulfide apparently is not, at least under these conditions.

Very few animals are capable of fixing any appreciable amounts of nitrogen gas from the atmosphere, other than termites and shipworms. To verifty that this pesticidal effect related to nitrogen-fixation ability, samples of molybdenum and tungsten compounds were fed, in dosages lethal to termites, to other pests such as fire ants, cockroaches and bark beetles. These pest insects were not killed by these compounds thus demonstrating that they are not broadly toxic to insect species. It is also known that molybdenum and tungsten compounds are relatively non-toxic to plants and to other animals, in contrast to many currently used termicidal agents which are broadly toxic to many organisms.

Thus, it can be readily appreciated that metallic salts and other effectively soluble compounds of molybdenum and tungsten exhibit significant and unusual toxicity to termites through some mechanism related to the ability to fix nitrogen. While it is believed that the mechanism of this toxicity is related to the mechanism for molybdenum uptake to create nitrogenase enzyme for the fixation of nitrogen, as stated, it is also possible that the toxicity mechanism results because of the strong reducing activity of the microflora gut. It is to be understood, therefore, that the present invention is not limited to the mechanism for this toxicity which is discussed here, but is instead directed toward both a composition for the control of nitrogen fixing pests including molybdenum or tungsten and a method for using these compositions to control pests regardless of the details of the mechanism by which they function.

It is envisioned that this termite control composition can be utilized in any conventional wood treating composition already containing fungicidal or other preservative compounds. The inclusion of a small amount of a molybdenum or tungsten metallic salt or derivative would also ensure that the treated wood would be safe from termite and shipworm infestation. Alternatively, these metallic salts for pest control could be incorporated in cellulosic pellets or baits which could be placed in pre-selected locations adjacent to the wood likely to be visited by the pests. A quantity of cellulosic material, such as wood, paper, paperboard, paper or paperboard products, or cotton, needs merely to be inoculated with a dose of a molybdenum or tungsten compound, and left as a bait in a location likely to be frequented by the pests. Alternatively, to protect wood structures such as housing, etc., molybdenum or tungsten compounds could be directly inoculated in the soil surrounding the structures. By use of such a bait, termites could be controlled in a structure regardless of whether or not the remaining wood in a structure to be protected was susceptible to treatment.

It is to be understood that a preferred method for using the compositions of the present invention is to impregnate the compositions directly into the wood to be protected. Such impregnated wood would be resistant to both termite and shipworm infestation. To be effective as a wood impregnant, the molybdenum compound must be in a form that prevents it from being immediately solubilized when the wood is exposed to water. One method would be to soak the wood in a highly soluble molybdenum (i.e. molybdate) solution under heat or pressure to introduce the compound into the wood. Wood with insoluble molybdenum impregnated therein would be particularly useful in marine applications where shipworms are a problem.

An alternative approach to introduce an relatively insoluble molybdenum compound into wood is to use a suspension of an insoluble compound as very fine particles which can be forced into wood pores under pressure. Another approach would be to use an organic solvent to dissolve a relatively water insoluble molybdenum compound to carry the compound into the wood.

It should be appreciated that a wide variety of concentrations of many molybdenum or tungsten compounds is possible within the spirit of the present invention as long as verifiable toxicity to termites and shipworms can be achieved. It is believed that the reasonable interpretation of the test data presented here is that any molybdenum or tungsten compound which is either effectively soluble in water or which otherwise makes its metal constituent biologically available to a pest when digested will be effective. By effectively soluble as used herein it is intended to mean compounds having some measurable solubility. By biologically available it is intended to mean compounds wherein the molybdenum or tungsten molecules are available for uptake by the host animals. From these parameters, it should be clear that a wide variety of salts and other compounds of each of these metals can be efficacious. It is also envisioned that such compositions in accordance with the present invention could be effectively used as soil inoculants in or around structures to be protected to prevent termite encroachment upon the structures through subterranean tunnelling.

It is understood that the present invention is not limited to the particular embodiments disclosed and illustrated herein, but embraces all such modified forms thereof as come within the scope of the following claims.

We claim:

1. A method for specifically controlling termites and shipworms which comprises
   treating cellulosic material with an effective amount of a soluble compound selected from the group consisting of sodium molybdate ($Na_2MoO_4$), molybdic anhydride ($MoO_3$), molybdic acid ($H_2MoO_4$), ferrous molybdate ($FeMoO_4$), sodium tungstate ($Na_2WO_4$), and di-ammonium molybdate (($NH_4)_2Mo_2O_7$) in a dosage sufficient to be toxic to termites and shipworms; and
   exposing the treated cellulosic material to the termites and shipworms to be controlled.

2. A method as claimed in claim 1 wherein the cellulosic material is treated with a soluble compound of molybdenum which is present at a concentration of greater than 50 parts per million.

3. A method as claimed in claim 1 wherein the cellulosic material is treated with sodium molybdate ($Na_2MoO_4$).

4. A method as claimed in claim 1 wherein the cellulosic material is treated with molybdic anhydride ($MoO_3$).

5. A method as claimed in claim 1 wherein the cellulosic material is treated with molybdic acid ($H_2MoO_4$).

6. A method as claimed in claim 1 wherein the cellulosic material is treated with ferrous molybdate ($FeMoO_4$).

7. A method as claimed in claim 1 wherein the cellulosic material is treated with sodium tungstate ($Na_2WO_4$) which is present at a concentration of greater than 90 parts per million.

8. A method as claimed in claim 1 wherein the cellulosic material is treated with di-ammonium molybdate ($(NH_4)_2Mo_2O_7$).

9. A method as claimed in claim 23 wherein the cellulosic material is wood.

10. A method as claimed in claim 1 wherein the cellulosic material is selected from the group consisting of paper, paperboard and products thereof.

11. A method for safeguarding a wood structure specifically from termites which comprises treating the soil around the structures with a termicidal concentration of a soluble compound selected from the group consisting of sodium molybdate ($Na_2MoO_4$), molybdic anhydride ($MoO_3$), molybdic acid ($H_2MoO_4$), ferrous molybdate ($FeMoO_4$), sodium tungstate ($Na_2WO_4$), and di-ammonium molybdate (($NH_4)_2Mo_2O_7$).

12. A composition for the specific control of termites and shipworms comprising
   a cellulosic carrier; and
   a termicidally effective amount of at least 50 parts per million of a soluble compound selected from the group consisting of sodium molybdate, molybdic anhydride, molybdic acid, ferrous molybdate, di-ammonium molybdate and sodium tungstate.

13. A composition as claimed in claim 12 wherein the cellulosic carrier is selected from the group consisting of paper, paperboard, paperboard products, and cotton.

* * * * *